United States Patent [19]

Russell et al.

[11] Patent Number: 4,968,127
[45] Date of Patent: Nov. 6, 1990

[54] CONTROLLABLE, VARIABLE TRANSMISSIVITY EYEWEAR

[76] Inventors: James P. Russell; Thomas J. Russell, both of 8601 W. 47th, Overland Park, Kans. 66203; Frank Mufich, 4241 SE. Wisconsin, Topeka, Kans. 66605

[21] Appl. No.: 443,876

[22] Filed: Nov. 30, 1989

Related U.S. Application Data

[63] Continuation of Ser. No. 275,440, Nov. 23, 1988, abandoned.

[51] Int. Cl.$^5$ .............................................. G02C 7/10
[52] U.S. Cl. ........................................ 351/44; 351/49; 351/158
[58] Field of Search .................. 351/41, 158, 44, 49; 350/330

[56] References Cited

U.S. PATENT DOCUMENTS

| | | |
|---|---|---|
| Re. 27,911 | 2/1974 | Dreyer . |
| 3,167,607 | 1/1965 | Marks et al. . |
| 3,236,651 | 2/1966 | Marks et al. . |
| 3,245,315 | 4/1966 | Marks et al. . |
| 3,475,765 | 11/1969 | Zeltmann . |
| 3,499,702 | 3/1970 | Goldmacher et al. . |
| 3,519,339 | 7/1970 | Hutchinson et al. . |
| 3,592,526 | 7/1971 | Dreyer . |
| 3,597,043 | 8/1971 | Dreyer . |
| 3,603,305 | 9/1971 | Oppenheimer . |
| 3,864,905 | 2/1975 | Richardson . |
| 3,942,870 | 3/1976 | Saeva . |
| 3,984,177 | 10/1976 | Trozzolo . |
| 4,005,928 | 2/1977 | Kmetz et al. . |
| 4,021,846 | 5/1977 | Roese . |
| 4,032,219 | 6/1977 | Constant et al. . |
| 4,039,803 | 8/1977 | Harsch . |
| 4,048,358 | 9/1977 | Shanks . |
| 4,066,335 | 1/1978 | Courtney et al. . |
| 4,279,474 | 7/1981 | Begorod . |
| 4,299,444 | 10/1981 | Romer . |
| 4,795,248 | 1/1989 | Okada et al. .................. 351/158 |

*Primary Examiner*—Rodney B. Bovernick
*Attorney, Agent, or Firm*—Hovey, Williams, Timmons & Collins

[57] ABSTRACT

Unique eyewear is disclosed having electronically controlled lens structures in which the optical transmissivity thereof is automatically adjusted to a level correlated with the level of ambient light. The preferred eyewear includes a pair of lens having liquid crystal material therebetween, a control circuit having a sensitivity-adjustable, ambient light sensor, and a power supply. The preferred power supply includes a battery and a photocell array distributed about the periphery of the lens structures. In use, the control circuit senses ambient light level and adjusts the transmissivity of the lens structure to a level correlated with the ambient light level.

12 Claims, 1 Drawing Sheet

CONTROLLABLE, VARIABLE TRANSMISSIVITY EYEWEAR

This is a continuation of copending application Ser. No. 275,440, filed on Nov. 23, 1988, now abandoned.

BACKGROUND OF THE INVENTION

1. Field of the Invention

The present invention is concerned with eyewear having electronically controlled lens structures in which the optical transmissivity thereof is automatically adjusted to a level correlated with the level of ambient light. More particularly, the present invention is concerned with eyewear in which a control circuit senses ambient light level and adjusts the transmissivity of the eyewear lens structures to a level correlated with the ambient light level.

2. Description of the Prior Art

Eyewear is known in the prior art which uses so-called PHOTOGRAY lens. These lens include a light-sensitive chemical structure which chemically darkens upon exposure to ambient light. The PHOTO-GRAY lens present a problem, however, in that with age, the sensitivity decreases thereby taking longer to respond to changes in ambient light levels. Additionally, the PHOTOGRAY lenses have a fixed sensitivity to ambient light, that is, have a fixed correlation with the level of ambient light.

The prior art also discloses electronically controlled lenses such as disclosed in U.S. Pat. Nos. 3,519,339, 3,245,315, and 4,039,803, the disclosures of which are hereby incorporated by reference. These prior art devices, such as that disclosed in the '315 patent, are designed to prevent eye damage from suddenly occurring high levels of ambient light in order to prevent flash blindness, for example. With this objective, these prior art devices devices are designed to automatically and quickly shift from a relatively transmissive condition to a relatively opaque condition upon the occurence of a high level of ambient light. These devices are not suitable, however, for use as day-to-day eyewear because they cannot produce varying levels of transmissivity correlated with varying levels of ambient light. Additionally, the prior art devices are powered solely by a battery pack which must be frequently replaced if the eyewear is frequently used.

SUMMARY OF THE INVENTION

The problems as outlined above are solved by the eyewear of the present invention. More particularly, the eyewear hereof provides structure which varys optical transmissivity correlated according to the sensed level of ambient light and which minimizes or eliminates battery replacement.

Broadly speaking, the preferred embodiment of the present invention includes a lens structure in which the optical transmissivity thereof is selectively and electronically adjustable, a framework coupled with the lens structure for wearing by a person in order to place the lens structure in an optical relationship with a person's eyes, and a control circuit, coupled with the lens structure and including means for coupling with the source of operating power, for sensing and responding to the level of ambient light and for electronically adjusting the transmissivity of the lens structure to a level correlated with the ambient light level.

The preferred eyewear includes a pair of the lens structures configured for placement respectively in front of the person's eyes. The lens structures include a pair of superposed lenses with liquid crystal material disposed therebetween. The preferred control circuit includes a phototransistor for sensing ambient light level and means for selectively varying the sensitivity of response to ambient light.

The preferred eyewear also includes a power source coupled with the control circuit for delivering operating power thereto. The preferred power source includes an array of photocells disposed about the periphery of the lens structure for converting ambient light into operating power for the control circuit. The preferred power source further includes a rechargable battery coupled with the photocell array for charging thereby.

Other preferred aspects of the present invention are disclosed hereinbelow.

BRIEF DESCRIPTION OF THE DRAWING FIGURES

DETAILED DESCRIPTION OF THE PREFERRED EMBODIMENTS

Figure 1:
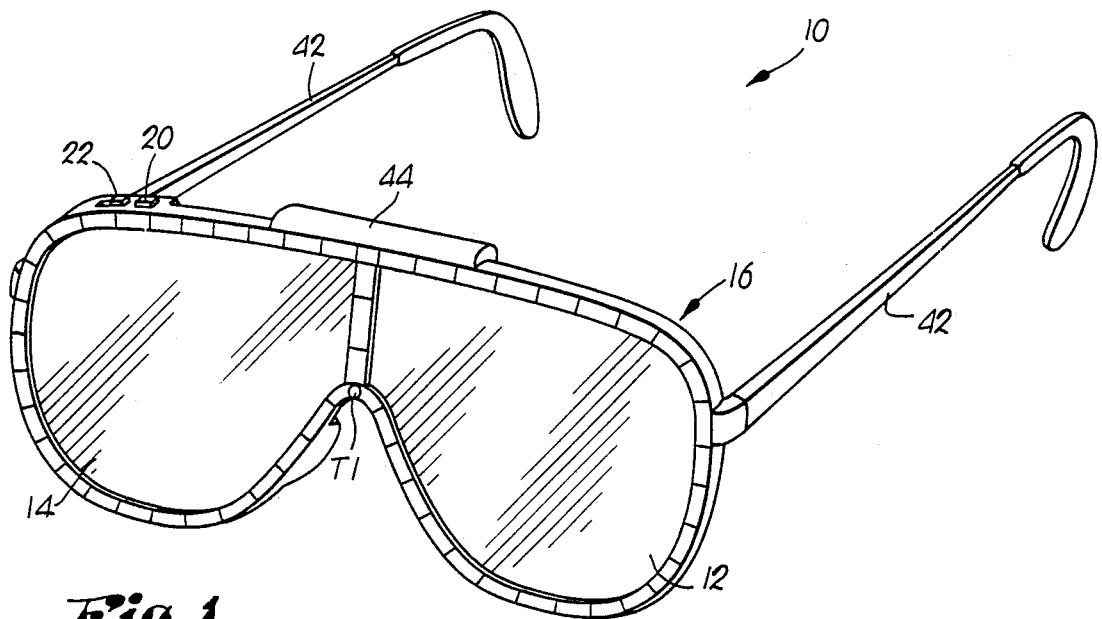
FIG. 1 is a perspective view of the preferred eyewear.

Referring now to the drawing figures, FIG. 1 illustrates a perspective view of the preferred eyewear 10 which includes a pair of left and right lens structures 12 and 14, framework 16, control circuit 18 (FIG. 3) which includes power switch 20 and sensitivity adjustment switch 22, and power supply 24 which includes battery 26 and photocell array 28.

Each lens structure 12, 14 includes a pair of polarizing lens 30 and 32 and liquid crystal assembly 34 which provide the optical means for selectively varying or adjusting the optical transmissivity of lens structures 12, 14. Although two lens structures are preferred, a single larger lens structure may be desirable in some applications or styles.

Figure 2:
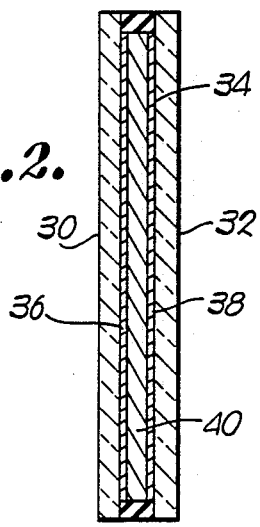
FIG. 2 is a sectional view of the preferred lens structure of the eyewear of FIG. 1.

As illustrated in the sectional view of FIG. 2, lenses 30, 32 are superposed with liquid crystal assembly 34 and photocell array 28 therebetween. In the preferred embodiment, photocell array 28 is adhered and sealed to the inboard surfaces of the periphery of lens 30 and 32 thereby forming a sealed boundary for liquid crystal assembly 34.

Assembly 34 includes a pair of transparent electrodes 36 and 38 respectively coating the interior surfaces of lens 30, 32 and liquid crystal material 40 therebetween. Liquid crystal material 40 advantageously may include dyes in order to present an apparent color as desired. As those skilled in the art appreciate, an electric field imposed across electrodes 36, 38 causes alignment of the liquid crystal molecules in material 40 which in turn alters the polarization of the light passing therethrough. The degree of alignment of the liquid crystals and the degree of light polarization, increases as the electric field strength, that is, the voltage, increases across electrodes 36, 38. In this way, the transmissivity of lens structures 12, 14 can be decreased or increased and thereby selectively varied or adjusted, by increasing or decreasing the voltage on electrodes 36, 38.

Framework 16 is configured in the preferred embodiment as a conventional eyeglass frame with a pair of temple pieces 42 configured to be worn by a person so that lens structures 12, 14 are presented respectively in front of the wearer's eyes in an optical relationship therewith. Framework 16 further includes control housing 44 for enclosing control circuit 18 and battery 26, and presents switches 20, 22 for access by the wearer as shown in FIG. 1. In the alternative, control circuit 18 could be manufactured in a configuration allowing it to be placed between lenses 30, 32 in a sealed relationship. Framework 16 can also take the form of goggles, or a helmet, for example, or other equivalent structure for placing the lens structure in an optical relationship with the wearer's eyes in order to control the level of ambient light transmitted thereto.

Figure 3:
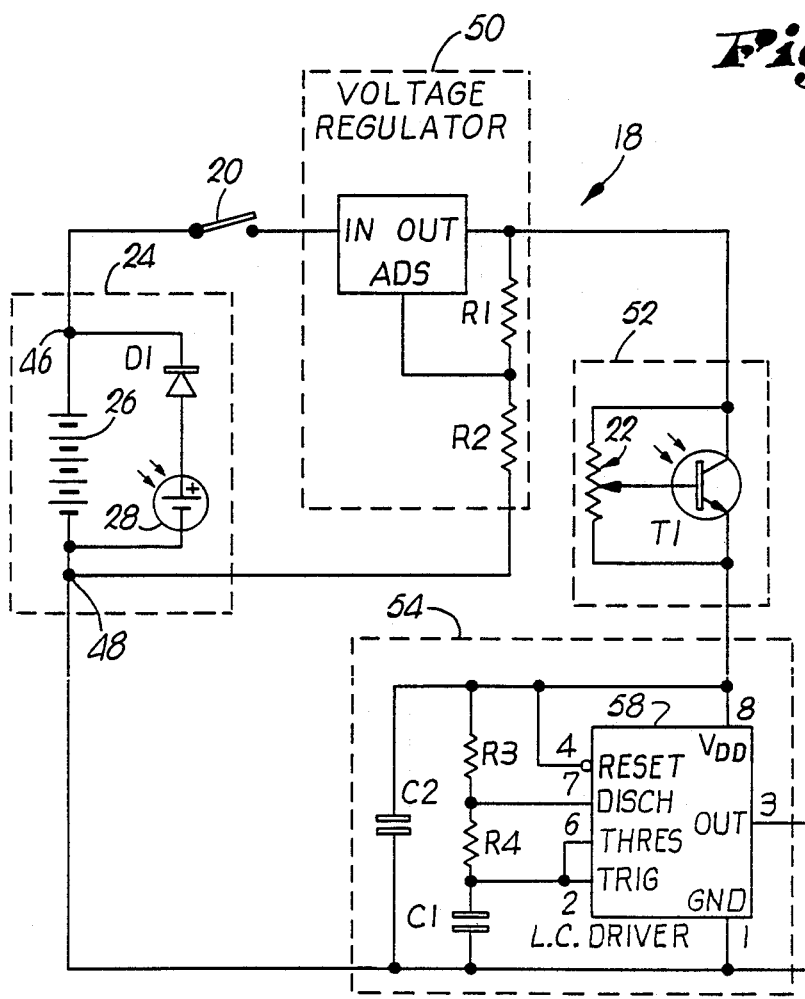
FIG. 3 is an schematic drawing illustrating the preferred control circuit and power supply of the eyewear.

FIG. 3 is an electrical schematic representation of control circuit 18 and power supply 24. In the preferred power supply 24, battery 26 and photocell array 28 selected to provide an output voltage at 7.2 V.D.C. Battery 26 is preferably a rechargable nickel cadmium battery. Photocell array 28 is coupled in parallel with battery 26 by way of diode D1 with the anode thereof coupled to the positive output terminal of array 28 and with the cathode thereof coupled with the positive terminal of battery 26 by way of terminal 46. The negative terminals of battery 26 by way of terminal 46. The negative common at terminal 48.

Photocell array 28 is preferably composed of a plurality of conventional photocells positioned around the periphery of lens structures 12, 14. Array 28 preferably presents sufficient capacity to supply all of the electrical power needs for control circuit 18 when exposed to ambient light sufficient to make light reduction to the wearer's eyes desirable. Additionally, photocell array 28 has enough excess capacity to charge battery 26 during these ambient conditions.

In the preferred embodiment, terminals 46 and 48 provide the means for coupling control circuit 18 with power supply 24.

Preferred control circuit 18 broadly includes power switch 20, voltage regulating circuit 50, ambient light sensing circuit 52, and liquid crystal driving circuit 54.

Power switch 20 is a conventional on/off switch coupled in series between terminal 26 and voltage regulating circuit 50 and is externally accessible by a wearer of eyewear 10 as illustrated in FIG. 1.

Voltage regulating circuit 50 is provided to ensure a stable operating voltage in the event of voltage fluctuations from power supply 24. Circuit 50 includes voltage regulator 51 (Type LM317) which receives input voltage at the preferred 7.2 V.D.C. at terminal IN thereof from power switch 21 when closed. Regulator 51 provides an output at terminal OUT which is connected to the voltage divider network composed of series connected resistors R1 (1.2 K ohms) and R2 (47 K ohms). The juncture between resistors R1 and R2 provides feedback to terminal ADJ of regulator 51. The other side of resistor R2 is connected to terminal 48.

Regulator 51 provides a stable output voltage at 6.4 V.D.C. to ambient light sensing circuit 52 which includes phototransistor T1 (type L1462) and sensitivity adjustment switch 22 which is in the form of an externally accessible, variable resistance potentiometer having a range of 100 K ohms Voltage from regulating circuit 50 is supplied at 6.4 V.D.C. to the collector of transistor T1 and to one side of switch 22. Switch 22 supplies biasing voltage to the base of transistor T1 according to the position thereof. The other side of adjustment switch 22 is connected to the emitter of transistor T1. Transistor T1 is preferably located in the vicinity of the nosepiece of eyewear 10 as shown in FIG. 1 in order to sense ambient light.

Transistor T1 provides an emitter output voltage between 0 and 6.0 V.D.C. correlated with the level of ambient light striking transistor T1. As the level of the ambient light striking transistor T1 increases, the output voltage at the emitter thereof increases to a maximum of 6.0 V.D.C. (allowing for a 0.4 V.D.C. drop across the transistor) when switch 22 supplies maximum biasing voltage to the transistor base.

Circuit 54 is included to provide a 50% duty cycle square wave at a 60 Hertz to lens structures 12, 14. The amplitude of the output square wave varies according to the supply voltage input from sensing circuit 52. As those skilled in the art will appreciate, liquid crystal material requires a reversing electric field to prevent permanent alignment of the liquid crystal molecules contained within liquid crystal material 40. Circuit 54 includes liquid liquid crystal driver 58 which is preferably a type TLC555 timer and further includes series connected resistors R3 (10 K ohms), R4 (100 K ohms), and capacitor C1 (0.1 u.F.). Additionally, capacitor C2 (10 u.F.) is connected in parallel across resistors R3, R4, and capacitor C1.

Driving circuit 54 receives the variable supply voltage provided by sensing circuit 52 at terminals 4 and 8 of driver 58, and to one side each of resistor R3 and capacitor R2 as shown in FIG. 3. The juncture between resistors R3 and R4 is connected to driver terminal 7 and the juncture between resistor R4 and capacitor C1 is connected to driver terminals 2 and 6. Driver terminal 1 and the other side of capacitor C1, C2, are connected to power supply terminal 48. Components R3, R4, C1 and C2 determine the preferred 60 Hertz, 50% duty cycle output from terminal 3 of driver 58.

Driver 58 supplies its output square wave at a voltage amplitude approximately the same at the input supply voltage but requires a minimum 2.8 V.D.C. supply voltage. Driver terminal 3 is connected to parallel-connected lens structures 12, 14 and specifically to respective electrodes 36 thereof. Electrodes 38 of lens structures 12, 14 are connected to power supply terminal 48.

In operation, sensing circuit 52 senses the level of ambient light and responds by providing supply voltage to driving circuit 54 correlated with the level of ambient light. In response, 58 provides its output square wave with a voltage amplitude correlated with the supply voltage amplitude which is in turn correlated with the level of ambient light sensed by transistor T1.

Liquid crystal material 40 responds to the voltage amplitude of the impressed square wave to change the polarization of the light passing therethrough. Thus, as the voltage amplitude increases, lens structures 12, 14 correspondingly reduce their respective transmissivity, that is, become darker. Conversely, as the ambient light striking transistor T1 decreases, sensing circuit 52 responds by decreasing its output supply voltage to driving circuit 54 which reduces the amplitude of the square wave delivered to lens structures 12, 14 thereby increasing the transmissivity of lens structures 12, 14 to allow more light to pass therethrough.

Sensitivity adjustment switch 22 allows the user to change the sensitivity of sensing circuit 52. This allows an individual wearer to increase or decrease the sensitivity in order to increase or decrease the transmissivity level of lens structures 12, 14 for a given ambient light level. In this way, each individual can adjust the transmissivity relative to a given ambient light level to suit individual taste.

As the above discussion reveals, the structure of eyewear 10 eliminates the need to don and remove eyewear 10 as ambient light conditions vary. This allows eyewear 10 to be worn at night while driving, for example, because eyewear 10 automatically adjusts to its highest transmissivity level but automatically reduces the transmissivity in the presence of oncoming bright lights. At night, with ambient light levels low, battery 26 provides the necessary operating power to control circuit 18.

As those skilled in the art will appreciate, the present invention encompasses many variations in the preferred embodiments herein described. For example, battery 26 could be a non-rechargeable battery such as lithium battery which would provide a very long life because the primary operating power is preferably supplied by photocells 28. Additionally, because of the capacity of photocell array 28, battery 26 could even be eliminated from the circuit if desired.

While voltage regulating circuit 50 is preferred as discussed above, it could be eliminated in some circumstances in which the supply voltage is sufficiently stable and additionally, could use other components than those preferred herein. For example, the voltage regulation could be provided by a combination of Zener diodes, capacitors, and resistors in order to provide a stable output voltage.

As those skilled in the art will also appreciate, the present invention is not limited to the use of a phototransistor for sensing the level of ambient light, but encompasses other devices providing equivalent function which might include, for example, photodiodes or the like.

As a final example, other materials are available which vary their transmissivity in response to electrical signals. These other materials include Kerr cells, Pockels cells, and the like. Such other optical materials may not require driving circuit 54 to provide a reversing electric field.

Having thus described the preferred embodiments of the present invention, the following is claimed as new and desired to be secured by Letters Patent:

We claim:

1. An eye shade apparatus for wearing by a person comprising:
   a lens structure in which the optical transmissivity thereof is electrically adjustable;
   a framework coupled with a lens structure for wearing by a person in order to place said lens structure in optical relationship with the person's eyes; and
   control circuit means, coupled with said lens structure and including means for coupling with a source of operating power, for sensing and responding to the level of ambient light and for electronically adjusting the transmissivity of said lens structure to a transmissive level correlated with said ambient light level for varying the amount of ambient light passing through said lens to the person's eyes.
   said lens structure including a pair of superposed lens having a liquid crystal material therebetween, said liquid crystal material being responsive to the application of a variable voltage thereto for correspondingly varying the amount of ambient light transmitted through said lens structure,
   said control circuit means including means for varying voltage applied to said liquid crystal material in response to varying levels of ambient light.

2. The apparatus as set forth in claim 1, further including two of said lens structures, said framework being configured for placing said structures in front of the respective eyes of a person when worn thereby.

3. The apparatus as set forth in claim 1, said control circuit means including a phototransistor for sensing said ambient light.

4. The apparatus as set forth in claim 1, said control circuit means including sensitivity varying means for selectively varying the sensitivity of response of said control circuit to said ambient light.

5. The apparatus as set forth in claim 4, said sensitivity varying means including a variable resistor.

6. The apparatus as set forth in claim 1, further including a power source coupled with said control circuit means for providing operating power thereto.

7. The apparatus as set forth in claim 6, said power source including photocell means for converting ambient light into operating power for said control circuit means.

8. The apparatus as set forth in claim 7, said photocell means including a plurality of photocells arranged about and within the periphery of said lens structure and sealed thereto.

9. The apparatus as set forth in claim 6, said power source including a battery.

10. The apparatus as set forth in claim 6, said power source including photocell means for converting ambient light into operating power for said control circuit means, and battery means for providing operating power to said control circuit means in the event of insufficient operating power from said photocell means, said photocell means presenting capacity sufficient to provide all of the operating power requirements of said control circuit means upon the occurrence of a predetermined minimum level of ambient light.

11. The apparatus as set forth in claim 10, said battery means including a rechargeable battery, said photocell means presenting sufficient capacity for supplying all of the operating power requirements of said control circuit means and for recharging said battery upon the occurrence of a predetermined minimum level of ambient light.

12. The apparatus as set forth in claim 1, said control circuit means further including voltage regulator means for receiving supply power from a source thereof and for providing regulated voltage output for operating said control circuit means.

* * * * *